(12) United States Patent
Towse et al.

(10) Patent No.: US 9,168,110 B2
(45) Date of Patent: Oct. 27, 2015

(54) DENTAL IMPLANT SYSTEM HAVING ENHANCED SOFT-TISSUE GROWTH FEATURES

(71) Applicant: Biomet 3i, LLC, Palm Beach Gardens, FL (US)

(72) Inventors: Ross W. Towse, Palm City, FL (US); Michael D. Scalise, West Palm Beach, FL (US); Zachary B. Suttin, West Palm Beach, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 144 days.

(21) Appl. No.: 13/781,889

(22) Filed: Mar. 1, 2013

(65) Prior Publication Data

US 2013/0323678 A1    Dec. 5, 2013

Related U.S. Application Data

(60) Provisional application No. 61/652,411, filed on May 29, 2012.

(51) Int. Cl.
*A61C 13/12* (2006.01)
*A61C 8/02* (2006.01)
*A61C 8/00* (2006.01)

(52) U.S. Cl.
CPC .............. *A61C 8/0006* (2013.01); *A61C 8/0066* (2013.01); *A61C 8/0074* (2013.01); *A61C 8/0078* (2013.01); *A61C 8/006* (2013.01); *A61C 2008/0046* (2013.01)

(58) Field of Classification Search
CPC .... A61C 8/005; A61C 8/0051; A61C 8/0069; A61C 8/0078; A61C 8/0013; A61C 8/0015

USPC ............................... 433/167, 172–176, 201.1
See application file for complete search history.

(56) References Cited

U.S. PATENT DOCUMENTS

| 4,439,152 A | 3/1984 | Small |
| 5,030,095 A | 7/1991 | Niznick |

(Continued)

FOREIGN PATENT DOCUMENTS

| CA | 2544768 | 5/2005 |
| DE | 4238383 | 7/1994 |

(Continued)

OTHER PUBLICATIONS

Atieh, M. A. "Platform Switching for Marginal Bone Preservation Around Dental Implants: A Systematic Review and Meta-Analysis." Journal of Periodontology. vol. 81, No. 10, Oct. 2010 (pp. 1350-1366).

(Continued)

*Primary Examiner* — Yogesh Patel
(74) *Attorney, Agent, or Firm* — Nixon Peabody LLP

(57) ABSTRACT

A dental implant system including an implant and an abutment is disclosed. The implant includes a generally cylindrical body, a central axis, a distal end for anchoring in a patient's bone and a proximal end opposing the distal end. The proximal end includes a roughened lateralized surface that surrounds an abutment-engaging region. The lateralized surface is disposed at a negative slope relative to the central axis. The abutment includes an upper portion for supporting a tooth-like prosthesis and a lower portion for engaging the abutment-engaging region of the dental implant. The diameter of the lower portion of the abutment is smaller than the diameter of the implant at its proximal end. The lower portion includes a first surface with a soft-tissue enhancing material. The first surface and the lateralized surface defining a circumferentially extending recess having a V-shaped cross-section for receiving and attachment to the soft tissue.

18 Claims, 4 Drawing Sheets

(56) References Cited

U.S. PATENT DOCUMENTS

| | | | |
|---|---|---|---|
| 5,310,343 A | 5/1994 | Hasegawa et al. | |
| 5,312,255 A | 5/1994 | Bauer | |
| 5,362,236 A | 11/1994 | Branemark | |
| 5,417,568 A | 5/1995 | Giglio | |
| 5,503,558 A | 4/1996 | Clokie | |
| 5,527,182 A | 6/1996 | Willoughby | |
| 5,564,925 A | 10/1996 | Shampanier | |
| 5,564,926 A | 10/1996 | Branemark | |
| 5,571,017 A | 11/1996 | Niznick | |
| 5,603,338 A | 2/1997 | Beaty | |
| 5,674,072 A | 10/1997 | Moser et al. | |
| 5,695,336 A | 12/1997 | Lazzara et al. | |
| 5,702,695 A | 12/1997 | Clokie | |
| 5,727,943 A | 3/1998 | Beaty et al. | |
| 5,759,034 A | 6/1998 | Daftary | |
| 5,785,525 A | 7/1998 | Weissman | |
| 5,863,201 A | 1/1999 | Lazzara et al. | |
| 5,876,453 A | 3/1999 | Beaty | |
| 5,890,902 A | 4/1999 | Sapian | |
| 5,897,319 A | 4/1999 | Wagner et al. | |
| 5,902,109 A | 5/1999 | Reams, III et al. | |
| 5,931,675 A | 8/1999 | Callan | |
| 5,947,735 A | 9/1999 | Day | |
| 6,102,703 A | 8/2000 | Day | |
| 6,164,969 A | 12/2000 | Dinkelacker | |
| 6,217,331 B1 | 4/2001 | Rogers et al. | |
| 6,217,333 B1 | 4/2001 | Ercoli | |
| 6,283,754 B1 | 9/2001 | Wohrle | |
| 6,394,809 B2 | 5/2002 | Rogers et al. | |
| 6,419,491 B1 | 7/2002 | Ricci et al. | |
| 6,431,869 B1 | 8/2002 | Reams, III et al. | |
| 6,454,569 B1 * | 9/2002 | Hollander et al. | 433/173 |
| 6,474,991 B1 | 11/2002 | Hansson | |
| 6,491,723 B1 | 12/2002 | Beaty | |
| 6,527,554 B2 | 3/2003 | Hurson et al. | |
| 6,652,765 B1 | 11/2003 | Beaty | |
| 6,655,961 B2 | 12/2003 | Cottrell | |
| 6,672,872 B2 | 1/2004 | Cottrell | |
| 6,720,855 B2 | 4/2004 | Vicci | |
| 6,776,617 B2 | 8/2004 | Lax | |
| 6,854,972 B1 | 2/2005 | Elian | |
| 7,059,855 B2 * | 6/2006 | Zickman et al. | 433/174 |
| 7,087,085 B2 | 8/2006 | Steinemann et al. | |
| 7,097,453 B1 | 8/2006 | Schroering, Jr. | |
| 7,169,317 B2 | 1/2007 | Beaty | |
| 7,291,013 B2 | 11/2007 | Aravena et al. | |
| 7,338,286 B2 | 3/2008 | Porter et al. | |
| 7,484,959 B2 | 2/2009 | Porter et al. | |
| 7,547,399 B2 | 6/2009 | Beaty | |
| 7,618,258 B2 | 11/2009 | Gogarnoiu | |
| 7,682,303 B2 | 3/2010 | Abolfathi | |
| 7,708,559 B2 | 5/2010 | Wohrle et al. | |
| 7,771,774 B2 | 8/2010 | Berckmans, III et al. | |
| 7,854,698 B2 | 12/2010 | Abolfathi | |
| 7,857,987 B2 | 12/2010 | Beaty | |
| 8,007,279 B2 | 8/2011 | Bassett et al. | |
| 8,029,283 B2 | 10/2011 | Schwarz et al. | |
| 8,048,345 B2 | 11/2011 | Feith | |
| 8,066,511 B2 | 11/2011 | Wohrle et al. | |
| 8,221,499 B2 | 7/2012 | Lazzara et al. | |
| 8,251,700 B2 | 8/2012 | Robb et al. | |
| 2003/0031982 A1 | 2/2003 | Abarno | |
| 2004/0033470 A1 | 2/2004 | Wohrle et al. | |
| 2005/0014108 A1 | 1/2005 | Wohrle et al. | |
| 2005/0106534 A1 | 5/2005 | Gahlert | |
| 2006/0188846 A1 | 8/2006 | Wohrle et al. | |
| 2006/0194170 A1 | 8/2006 | Wohrle et al. | |
| 2006/0246398 A1 | 11/2006 | Groll et al. | |
| 2006/0292523 A1 | 12/2006 | Elian | |
| 2007/0202462 A1 | 8/2007 | Schwarz et al. | |
| 2007/0298379 A1 | 12/2007 | D'Alise | |
| 2008/0057475 A1 | 3/2008 | Feith | |
| 2008/0153064 A1 | 6/2008 | Han et al. | |
| 2008/0213728 A1 | 9/2008 | Rhew | |
| 2008/0233539 A1 | 9/2008 | Rossler et al. | |
| 2008/0293012 A1 | 11/2008 | Chaves et al. | |
| 2009/0061389 A1 | 3/2009 | Lomicka et al. | |
| 2009/0111072 A1 * | 4/2009 | Lombardo et al. | 433/174 |
| 2009/0239195 A1 | 9/2009 | Wohrle et al. | |
| 2009/0280454 A1 | 11/2009 | Hanna | |
| 2009/0305193 A1 | 12/2009 | Han et al. | |
| 2010/0081109 A1 | 4/2010 | Schlottig et al. | |
| 2010/0151421 A1 * | 6/2010 | Devengencie et al. | 433/174 |
| 2010/0179665 A1 | 7/2010 | Schlottig et al. | |
| 2010/0196850 A1 | 8/2010 | Konig | |
| 2010/0196851 A1 | 8/2010 | Konig | |
| 2010/0196852 A1 * | 8/2010 | Baruc et al. | 433/173 |
| 2010/0330530 A1 | 12/2010 | Menzel et al. | |
| 2011/0014586 A1 | 1/2011 | Jorneus et al. | |
| 2011/0045439 A1 | 2/2011 | Tripodakis et al. | |
| 2011/0076643 A1 | 3/2011 | Kahdemann | |
| 2011/0081626 A1 | 4/2011 | Hurson | |
| 2011/0104638 A1 | 5/2011 | Schlottig et al. | |
| 2011/0117522 A1 | 5/2011 | Verma et al. | |
| 2011/0123951 A1 | 5/2011 | Lomicka | |
| 2011/0123953 A1 | 5/2011 | Jorneus et al. | |
| 2011/0129799 A1 | 6/2011 | Kwan | |
| 2011/0136077 A1 | 6/2011 | De Moyer | |
| 2011/0151407 A1 | 6/2011 | Canullo | |
| 2011/0166670 A1 | 7/2011 | Lyngstadaas et al. | |
| 2011/0171602 A1 | 7/2011 | Schlottig et al. | |
| 2011/0183291 A1 | 7/2011 | Malo Carvalho et al. | |
| 2011/0200969 A1 | 8/2011 | Schroering | |
| 2011/0287381 A1 | 11/2011 | Sanders | |
| 2011/0300510 A1 | 12/2011 | Heo | |

FOREIGN PATENT DOCUMENTS

| | | |
|---|---|---|
| EP | 0388576 | 9/1990 |
| EP | 0438984 | 7/1991 |
| EP | 1529497 | 5/2005 |
| WO | WO 2010004605 A2 | 1/2010 |

OTHER PUBLICATIONS

Bateli, M. "Implant Neck Configurations for Preservation of Marginal Bone Level: A Systematic Review." The International Journal of Oral & Maxillofacial Implants. vol. 26, No. 2, Mar. 2011 (pp. 290-303).

Brunski, John B. "In Vivo Bone Response to Biomechanical Loading at the Bone/Dental-Implant Interface." Advances in Dental Research. No. 13, Jun. 1999 (pp. 99-119).

Gardner, D. M. "Platform Switching as a Means to Achieving Implant Esthetics." New York State Dental Journal. vol. 71, No. 3, Apr. 2005 (pp. 34-37).

Lazzara, R. J. et al. "Platform Switching. A New Concept in Implant Dentistry for Controlling Postrestorative Crestal Bone Levels." The International Journal of Periodontics & Restorative Dentistry. vol. 26, No. 1, Feb. 2006 (pp. 9-17).

Lopez-Mari, L. et al. "Implant Platform Switching Concept: An Updated Review." Medicina Oral Patologia Oral y Cirugia Bucal. vol. 14, No. 9, Sep. 2009 (pp. 450-454).

Serrano-Sanchez, P. R. et al. "The Influence of Platform Switching in Dental Implants: A Literature Review." Medicina Oral Patologia Oral y Cirugia Bucal. vol. 16, No. 3, May 2011 (pp. 400-405).

Annex to Form PCT/ISA/206 Communication Relating to the Results of the Partial International Search related to PCT/US2013-039250, mailed Sep. 19, 2013.

* cited by examiner

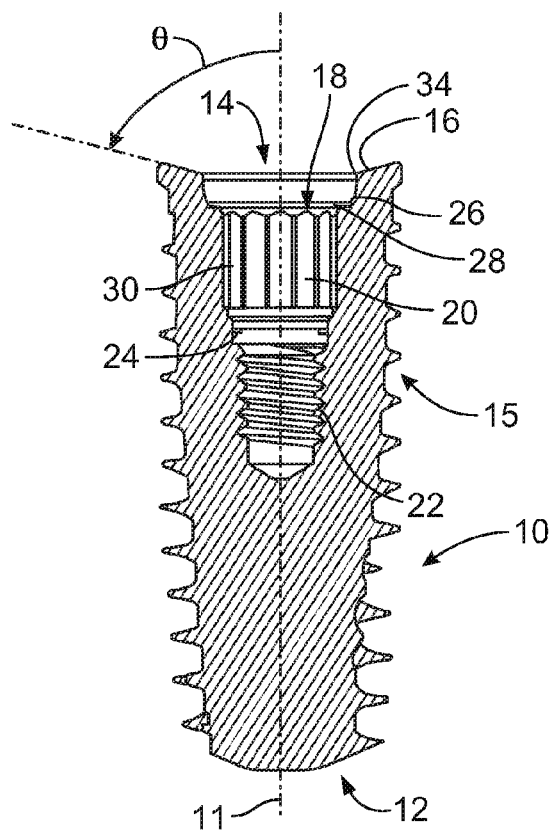
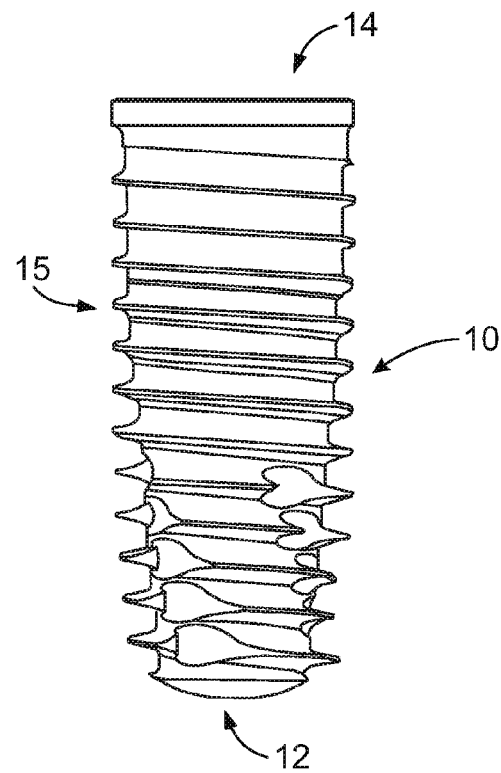
FIG. 1A  FIG. 1B
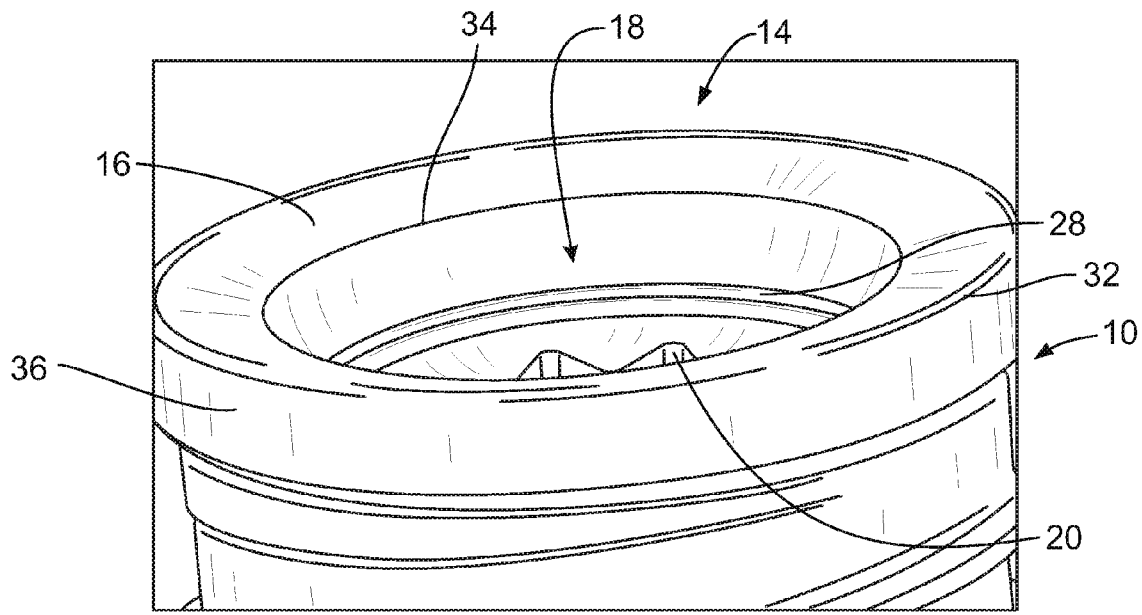
FIG. 1C

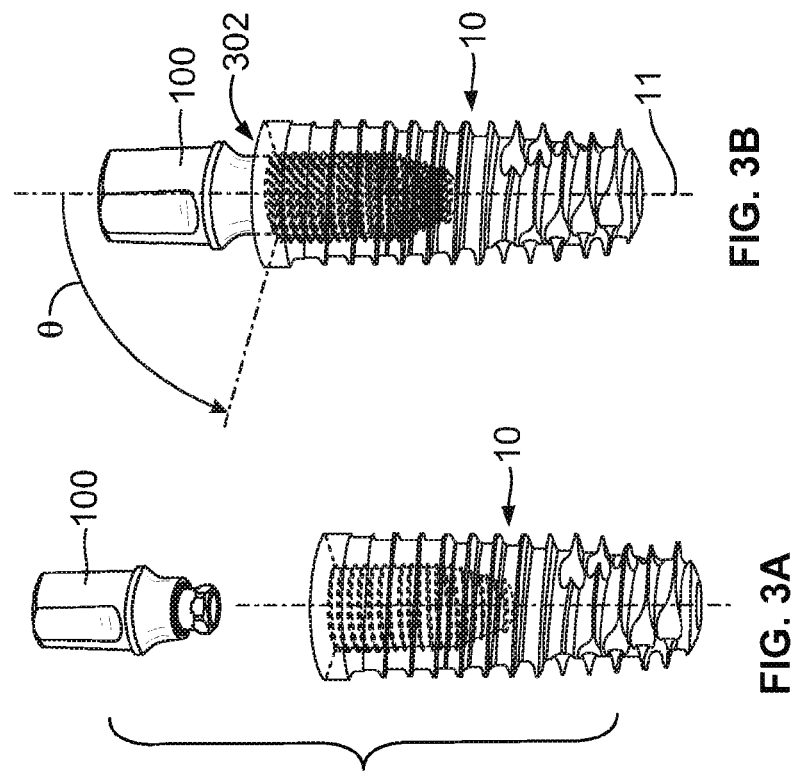
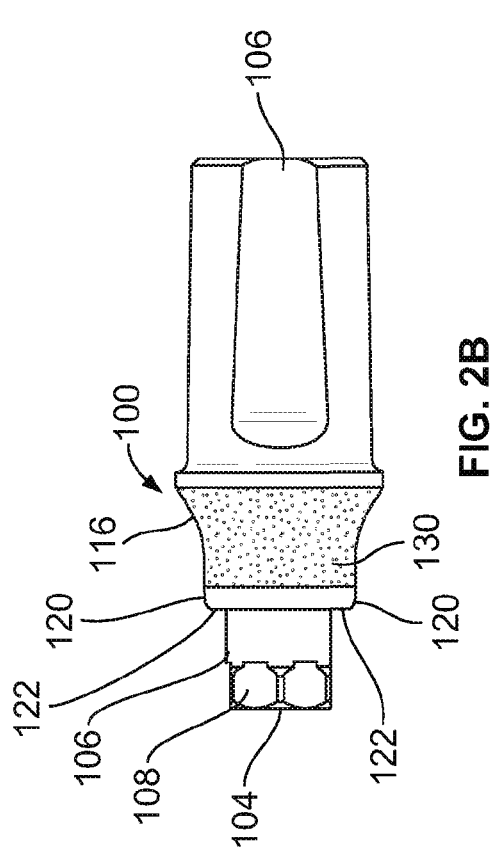
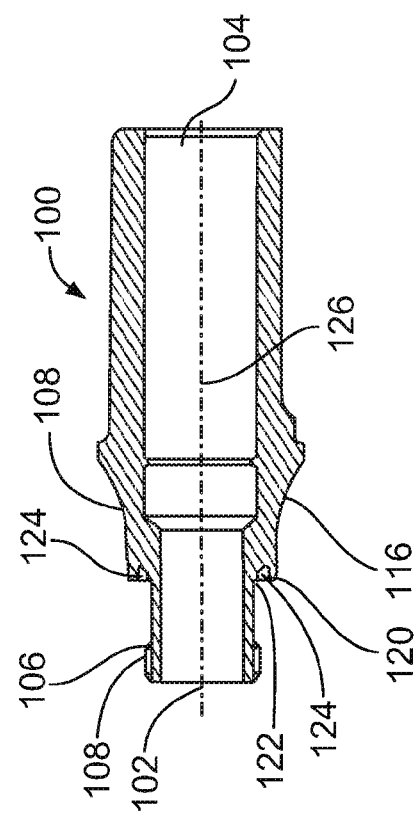

DENTAL IMPLANT SYSTEM HAVING ENHANCED SOFT-TISSUE GROWTH FEATURES

CROSS-REFERENCE TO RELATED APPLICATION

This application claims the benefit of U.S. Provisional Application No. 61/652,411, filed May 29, 2012, which is hereby incorporated by reference herein in its entirety.

TECHNICAL FIELD

This disclosure relates to restorative dental implants and abutments.

BACKGROUND

Single tooth restorations present the unique requirement that they must be supported non-rotationally on an underlying abutment. When a prepared natural tooth is the underlying abutment, this requirement is met in the normal course of preparing the abutment with a non-circular cross-section. Likewise, when the underlying abutment is a post fitted onto an implant, this requirement is met by preparing the post with a noncircular cross-section. This latter scenario can be more complicated due to the added connection between the implant and the abutment.

Typically, a dental implant is implanted into the bone of a patient's jaw and comprises a socket, e.g., a bore, which is accessible through the overlying or surrounding gum tissue for receiving and supporting one or more attachments or components which, in turn, are useful to fabricate and support the prosthodontic restoration. Under current dental implant techniques, dental implant procedures typically involve a threaded implant that is screwed into the bone tissue. However, the present disclosure is not concerned with the implant modality that is used. The disclosure is, however, concerned with the implant-abutment interface, as well as with other matters.

While numerous design iterations have been marketed, overall there have been two types of implant-abutment interfaces within these assemblies: an external connection implant and an internal connection implant. The external hexagonal implant design typically has a hexagonal boss (or another anti-rotation feature) protruding out of the implant's upper surface and the corresponding abutment has a female anti-rotational receptacle. The upper surface below the hexagonal boss engages the abutment. The hexagonal boss acts to constrain the abutment from rotating around the longitudinal axis as well as preventing movement on the plane coincident with the implant seating surface. Unfortunately, such an interface has very little stability until the screw is introduced and fully seated between the abutment and the implant. The screw is essentially the sole component resisting bending forces.

In contrast, the internal connection implant design has an anti-rotational female member or socket (e.g., a hexagonal anti-rotation feature) located below the implant's upper surface, and the corresponding abutment has a male protrusion. The abutment is typically seated on the upper surface as the external hexagonal design, the only difference being that the anti-rotation feature on the implant is located below this surface. The benefit of this system is that it has intrinsic stability without the screw, and then experiences increased stability once the screw is introduced and fully seated. The system responds in a more unified manner to bending forces. While this system has advantages over the external hex implant, one disadvantage (which applies to the external hex as well) is that it is prone to leak at the implant-abutment interface (seating surface) due to "lifting" of the abutment under load that may create an intermittent gap resulting in bacteria penetration and subsequent crestal bone loss.

It is known in the art to include, at the proximal end of the implant, a lateralized surface surrounding the area where the abutment sits within the implant. In such designs, the diameter of the implant at its proximal end is larger than the diameter of the abutment in an attempt to inhibit crestal bone remodeling, i.e., the implant system is platform-switched. It is also known in the art to include a lateralized surface that is disposed at a positive slope relative to the central axis, such that the lateralized surface tapers downwardly away from the uppermost region of the central bore of the implant. One example is U.S. Pat. No. 6,394,809 to Rogers et al., where an outer surface tapers in a positive direction from a maximum diameter region to a smaller diameter region. Another example includes U.S. Pat. Pub. No. 2006/0246398 to Groll et al., where the implant includes a step in the middle of the top surface, with the general flow being in a positive direction from a maximum diameter region to the smaller diameter step region. In dental implant systems, small microgaps between the implant and the abutment might be present, even if the implant and the abutment are tightly sealed. Fluids may enter the small microgaps between the implant and the abutment, which is undesirable. In these known systems, the positive slope of the lateralized surface tends to inhibit fluids from flowing downwardly toward the central bore of the implant and into the micrograps between the implant and the abutment.

BRIEF SUMMARY

In one aspect of the present invention, a dental implant system includes a dental implant and an abutment. The dental implant includes a generally cylindrical body, a central axis, a distal end for anchoring into a patient's bone and a proximal end opposing the distal end. The proximal end includes a lateralized surface surrounding an abutment-engaging region. The lateralized surface defines a soft-tissue attachment interface and is roughened to promote soft-tissue attachment. The lateralized surface is disposed at a negative slope relative to the central axis. The abutment has an upper portion for supporting a tooth-like prosthesis and a lower portion for engaging the abutment-engaging region of the dental implant. The lower portion has a diameter that is smaller than a diameter of the implant at the proximal end. The lower portion includes a first surface with a soft-tissue enhancing material. The first surface of the lower portion of the abutment and the lateralized surface of the dental implant define a circumferentially extending recess having a V-shaped cross section for receiving and attachment to the soft tissue.

In another aspect of the present invention, a dental implant system includes a dental implant and an abutment. The dental implant includes a generally cylindrical body, a central axis, a distal end for anchoring into a patient's bone and a proximal end opposing the distal end. The proximal end includes a lateralized surface surrounding an abutment-engaging region. The lateralized surface defines a soft-tissue attachment interface and lacks any sharp angles or corners to prevent abrading of the soft tissue. The lateralized surface is disposed at a negative slope relative to the central axis. The abutment has an upper portion for supporting a tooth-like prosthesis and a lower portion for engaging the abutment-engaging region of the dental implant. The lower portion has a diameter that is smaller than a diameter of the implant at the proximal end. The lower portion includes a first surface with a soft-tissue enhancing material. The first surface of the lower portion of the abutment and the lateralized surface of the dental implant define a circumferentially extending recess having a V-shaped cross section for receiving and attachment to the soft tissue.

In a further aspect of the present invention, a dental implant for use in conjunction with an abutment includes a generally cylindrical body, a central axis, a distal end for anchoring in a patient's bone and a proximal end opposing the distal end. The proximal end includes a lateralized surface surrounding an abutment-engaging region. The lateralized surface defines a soft-tissue attachment interface and is roughened to promote soft-tissue attachment. The lateralized surface is disposed at a negative slope relative to the central axis.

Another disclosed aspect is the dental implant for use in conjunction with an abutment. The dental implant includes a generally cylindrical body, a central axis, a distal end for anchoring in a patient's bone and a proximal end opposing the distal end. The proximal end includes a lateralized surface surrounding an abutment-engaging region. The lateralized surface is a planar surface that lacks steps and sharp corners and defines a soft-tissue attachment interface. The lateralized surface is disposed at a negative slope relative to the central axis.

The foregoing and additional aspects and implementations of the present invention will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 1A is a cross-section side view of an implant with a vertical abutment interface;

FIG. 1B is a side view of the implant shown in FIG. 1A;

FIG. 1C is a perspective view of the implant shown in FIG. 1A;

FIG. 2B is a side view of the abutment shown in FIG. 2A;

FIG. 2C is a cross-section side view of the abutment shown in FIG. 2A;

FIG. 3A is a perspective view of a dental implant system including an implant and an abutment;

FIG. 3B is a perspective view of the dental implant system of FIG. 3B when the abutment is seated in the implant;

Figure 1D:
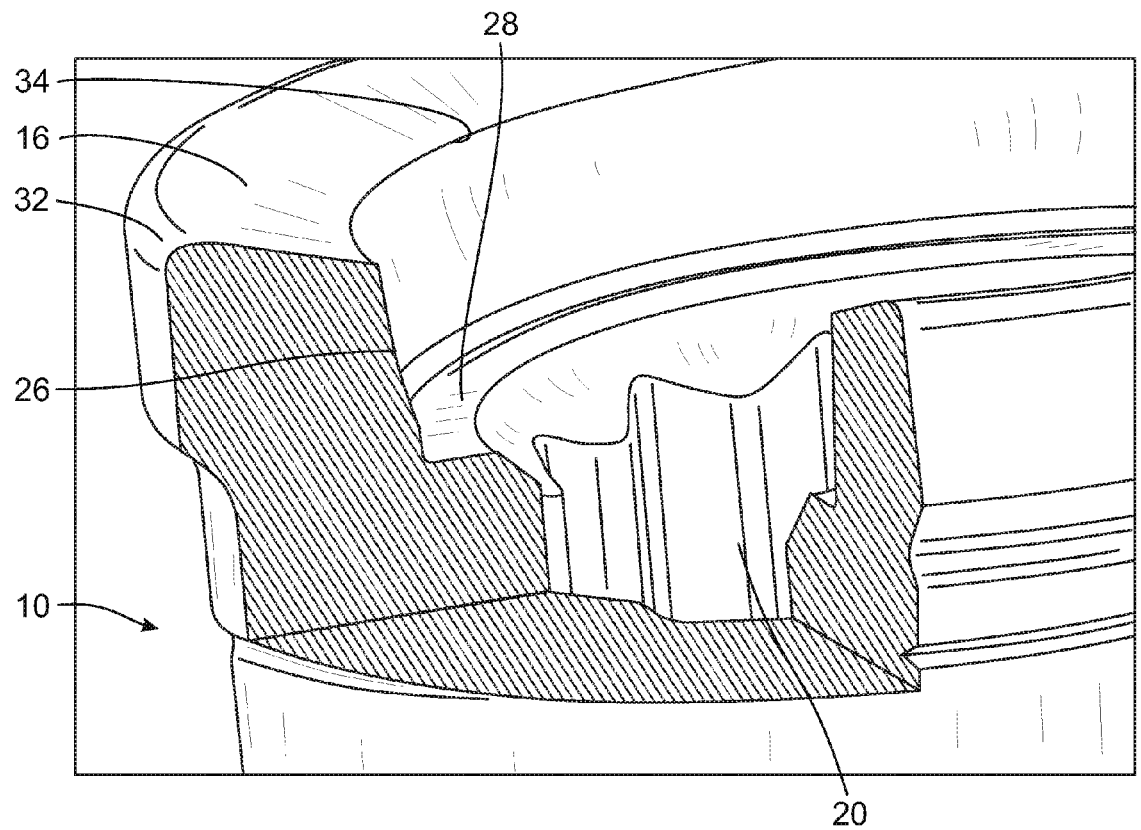
FIG. 1D is a perspective cutaway view of the implant shown in FIG. 1A.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

FIG. 1A is a cross-section side view of an implant 10 with a vertical abutment interface. The implant 10 is typically constructed of titanium or alloys thereof. The implant 10 includes a central axis 11, a distal end 12, a proximal end 14 opposing the distal end 12, and at least one thread 15 disposed therebetween for screwing the implant 10 into the bone of a patient. The proximal end 14 includes a lateralized surface 16 that is disposed at a negative slope relative to the central axis 11. The negative slope is defined by an angle θ. The slope is considered negative when the angle θ is less than 90°. The slope is considered positive when the angle θ is greater than 90°. As shown, the angle θ is about 45°. In another embodiment, the angle θ is between about 30° and about 60°. The lateralized surface 16 extends circumferentially and surrounds an interior bore 18 adapted to engage the abutment 100 of FIG. 2A when the abutment 100 is fully seated in the implant 10. The abutment 100 is typically constructed of titanium, including alloys thereof, or titanium nitride. The abutment 100 may also be constructed of ceramic, or a variety of polymers.

The lateralized surface 16 defines a soft-tissue attachment interface. The lateralized surface 16 may be roughened to promote soft-tissue attachment. The lateralized surface 16 may be roughened by any known methods, including laser treatment, etching, acid etching, mechanical etching, sandblasting, plasma treatment, or any combination thereof. Mean roughness of the lateralized surface 16 is preferably between about 1.3 and about 3.0 microns. Alternatively, the lateralized surface 16 may be micro-machined (e.g., a turning or lathing operation) with microgrooves. The microgrooves may have the dimensions of about 10 microns peak-to-peak and about 10 microns peak-to-valley. According to another embodiment, the lateralized surface 16 may be machined smooth.

The interior bore 18 extends distally from the proximal end 14 towards the distal end 12. The interior bore 18 includes a first anti-rotation cavity 20 and a threaded region 22 distal of the first anti-rotation cavity 20. A counter bore 24 is formed between the first anti-rotation cavity 20 and the threaded region 22.

The interior bore 18 includes an annular inner surface 26 proximate the first anti-rotation cavity 20. The annular inner surface 26 transitions to a flat vertical stop surface 28 that borders the first anti-rotation cavity 20. As will be explained below, the annular inner surface 26 and the flat vertical stop surface 28 function to guide the abutment 100 of FIG. 2A and prevent vertical location variability of the abutment 100 relative to the implant 10. The tight contact of the abutment 100 at the annular inner surface 26 and the flat vertical stop surface 28 also forms a seal to minimize gaps in the interface between the implant 10 and the abutment 100. The flat vertical stop surface 28 provides a positive limit to the axial movement of the abutment 100 towards the distal end 12 of the implant 10. According to another aspect of the present invention, the annular inner surface 26 may transition to a circumferentially-extending recess and the abutment 100 may include a radial ledge, lip, or rib that is configured to fit into the circumferentially-extending recess for sealing.

Focusing on FIGS. 1A and 1D, the first anti-rotation cavity 20 of the implant 10 includes a multi-sided interior surface 30. The multi-sided interior surface 30 has a plurality of obtuse interior angles in a double hexagonal shape, but other socket shapes may be used. The threaded region 22 accepts an abutment screw 106 in FIG. 2A.

The first anti-rotation cavity 20 is typically adapted to mate with a conventional driving tool, for example, a tool with a working end comprising a square, a pentagon, a hexagon, an octagon, etc. However, another cavity may be included in the implant instead of the first anti-rotation cavity 20.

Focusing on FIG. 1C, an exploded perspective view of the implant shown in FIG. 1A is shown. The implant includes an interior bore 18 surrounded by the lateralized surface 16. The lateralized surface 16 has a rounded outer circumferentially extending surface 32. The rounded outer circumferentially extending surface 32 is rounded to prevent any abrasion or other harm to soft tissue and to achieve superior clinical results and patient satisfaction. The lateralized surface 16 does not have any sharp angles or corners to prevent abrading the soft tissue. As shown, the lateralized surface 16 is non-supportive of the abutment 100. In other words, the lateralized surface 16 does not provide any positive support for retaining the abutment 100. Thus, the abutment 100 is fully supported by the elements of the implant 10 located in the interior bore 18. The lateralized surface 16 and the annular inner surface 26 meet at a ledge 34 that is in contact with the abutment 100. The lateralized surface 16 is a planar surface disposed from the rounded outer circumferentially extending surface 32 to the ledge 34 abutting the interior bore 18 as shown in FIGS. 1A and 1C to achieve superior clinical results and patient satisfaction. In an alternative embodiment, the lateralized surface 16 has a slight curvature and is a convex or a concave surface. The implant 10 includes an exterior collar section 36 that extends in a distal direction from the outer circumferentially extending surface 32. A portion of the collar section 36 may be roughened.

Figure 2A:
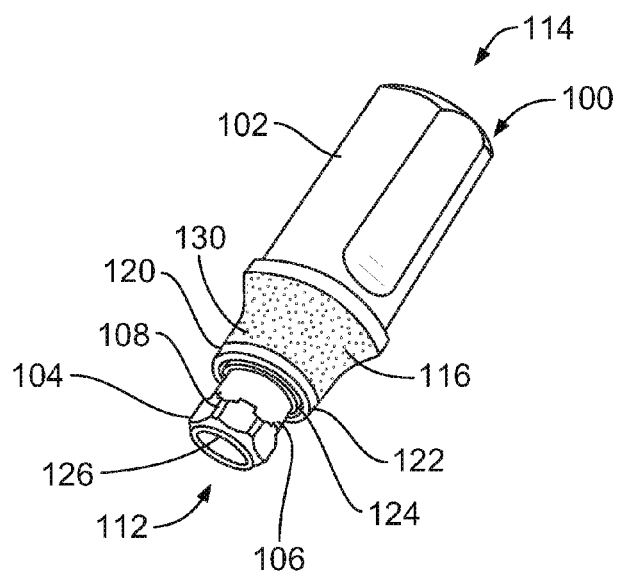
FIG. 2A is a perspective view of an abutment with a vertical implant interface.

In FIGS. 2A-2C, the abutment 100 includes a post 102 located within an upper section 114 and a stem 104 located within a lower section 112 extending in a relative downward direction from the post 102. The stem 104 includes a locking portion 106 configured to be positioned in the first anti-rotation cavity 20 when the abutment 100 is positioned in the implant 10. Accordingly, the locking portion 106 has a multi-sided exterior surface 108 that is adapted to rotationally-lockingly engage the interior multi-sided interior surface 30 of the first anti-rotation cavity 20 of implant 10 in FIG. 1D, such that the abutment 100 is prevented from rotating relative to the implant 10.

The abutment 100 includes a transitional section 116 positioned between the post 102 and the stem 104. The transitional section 116 is generally conical in shape with a larger end connected to the post 102 and an opposite smaller end connected to the stem 104. The transitional section 116 may be of any suitable shape. The annular inner surface 26 of the implant 10 is configured to form a seal with the transitional section 116 of the abutment 100. The transitional section 116 includes a soft-tissue contact zone 130. The soft-tissue contact zone 130 may be coated or enhanced with a suitable soft-tissue enhancing material. The soft-tissue enhancing material may be collagen or, such as the collagen on a titanium implant described in U.S. Pat. No. 6,524,718, the disclosure of which is hereby incorporated by reference in its entirety. The soft-tissue enhancing material may also be a combination of two or more soft-tissue enhancing materials. The lateralized surface 16 may also include collagen. The soft-tissue contact zone 130 may also be roughened.

The smaller end of the transitional section 116 mates with the interior bore 18 of the implant 10 in FIGS. 1A-1D. The transitional section 116 includes an outer surface that has a curved shape from the larger end with the larger diameter closest to the post 102 to the opposite end with a smaller diameter connected to the stem 104. A slightly curved outer surface 120 terminates at the smaller end of the transitional section 116 and has the same general dimension and shape as the annular inner surface 26 of the implant 10. According to another aspect of the present invention, the outer surface 120 may be straight or substantially straight. The outer surface 120 forms a circular vertical stop surface 122 for abutting the flat vertical stop surface 28 of the implant 10. The circular vertical stop surface 122 includes a circular groove 124 that is cut into the transitional section 116. The circular groove 124 may be cut to a depth of 0.010 to 0.020 inches or deeper or shallower if desired. Alternatively, the circular groove 124 may be cut to any suitable depth.

In the abutment 100, a through-bore 126 extends through the post 102, the stem 104, and the transitional section 116 to allow an abutment screw to be inserted therein. The abutment screw is inserted into the through-bore 126 in the abutment 100 to threadably engage the threads of the threaded region 22 of the implant 10 as shown in FIG. 1A.

A further benefit of better compliance is realized via the groove 124 on the abutment 100. The groove 124 allows a more compliant interface of the abutment 100 with the implant 10. Due to the groove 124, the interface formed by the outer surface 120 of the transitional section 116 has built in flexibility to compress into the groove 124 to allow the outer surface 120 to better conform to the radially curved inner surface 30 of the implant 10 and in turn increase the seal contact area between the abutment 100 and the implant 10. This flexibility is achieved by removing material from the cross-section of transitional section 116 of the abutment 100 to form the groove 124. Further, because the abutment 100 is compliant with the implant 10, the design may be manufactured more robustly, as the system will work under a wider range of tolerance configurations.

Figure 3C:
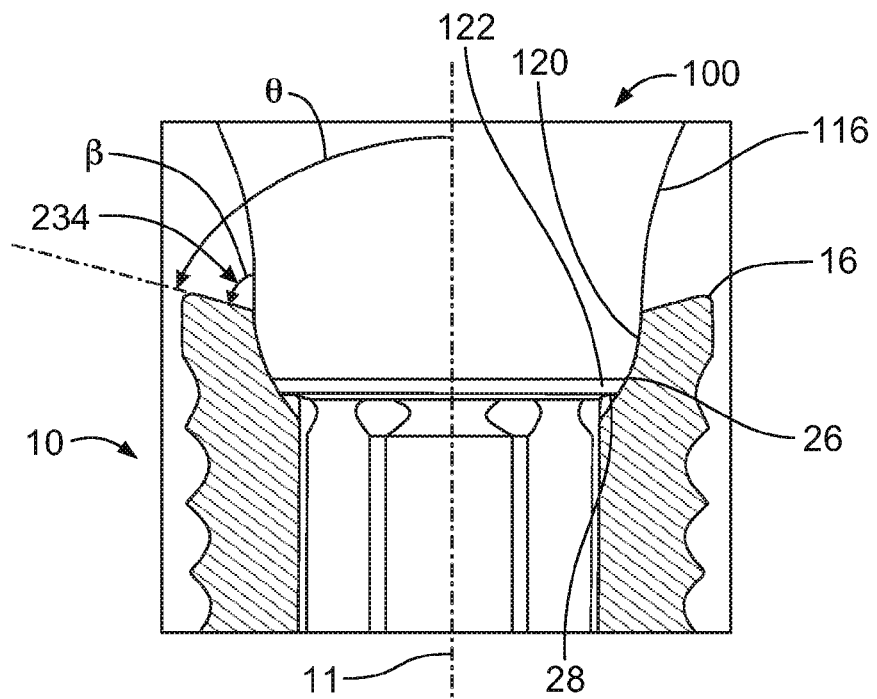
FIG. 3C is a perspective side cutaway view of the final contact between abutment and implant in FIGS. 3A and 3B when the abutment is seated in the implant.

The combination of the outer surface 120 and the vertical stop surface 122 allows for a seal between abutment 100 and the implant 10. The vertical stop surface 122 contacts the flat vertical stop surface 28 of the abutment 10, which prevents vertical location variability of the abutment 100 relative to the implant 10. The insertion of the abutment 100 in the implant 10 is shown with reference to FIGS. 3A-3D. FIG. 3C is a perspective side cutaway view of the final contact between the abutment 100 and the implant 10. For convenience of illustration, the groove 124 has been omitted from FIG. 3C. As shown in FIG. 3C, the outer surface 120 contacts the annular inner surface 26 of the implant 10, and the vertical stop surface 122 contacts the flat vertical stop surface 28 of the implant 10.

Referring now to FIG. 3C, the transitional surface 116 of the abutment 100 and the lateralized surface 16 of the dental implant 10 define a circumferentially extending recess 234 having a V-shaped cross section for receiving and attachment to the soft tissue. The circumferentially extending recess 234 is substantially open, such that there are no surfaces obstructing or preventing the soft tissue from growing onto the surfaces defining the circumferentially extending recess 234, which are preferentially treated for improved soft tissue retention. The circumferentially extending recess 234 has to be of an appropriate size such that a sufficient amount of soft tissue may grow therein. The angle β of the circumferentially extending recess 234 (as measured about halfway up the axial length of the recess 234) may vary in size and is typically between about 30° and about 60°, preferably about 45° In another embodiment, the angle β is about 75°. The circumferentially extending recess 234 does not include any sharp angles or steps that may abrade the soft tissue during micromovement associated with chewing. Importantly, the surfaces 116 and 16 forming the circumferentially extending recess 234 do not have any grooves or ridges thereon, such that there are no barriers to soft tissue growth and attachment.

As shown in FIGS. 3A and 3B, at the implant-abutment interface 302, the diameter of the implant 10 (diameter at the outer edge of the lateralized surface 16) is between about 2.5 mm and about 10 mm and is larger than the diameter of the abutment 100. The diameter of the abutment 100 at the inside edge of the lateralized surface 16 is between about 2 and about 9.5 mm. The mismatch between the diameter of the implant 10 and the diameter of the abutment 100 at interface 302 may be between about 0.25 mm and about 6.5 mm, and preferably between 1.5 mm and 3.0 mm, so as to create a platform-switched dental implant system.

Figure 4:
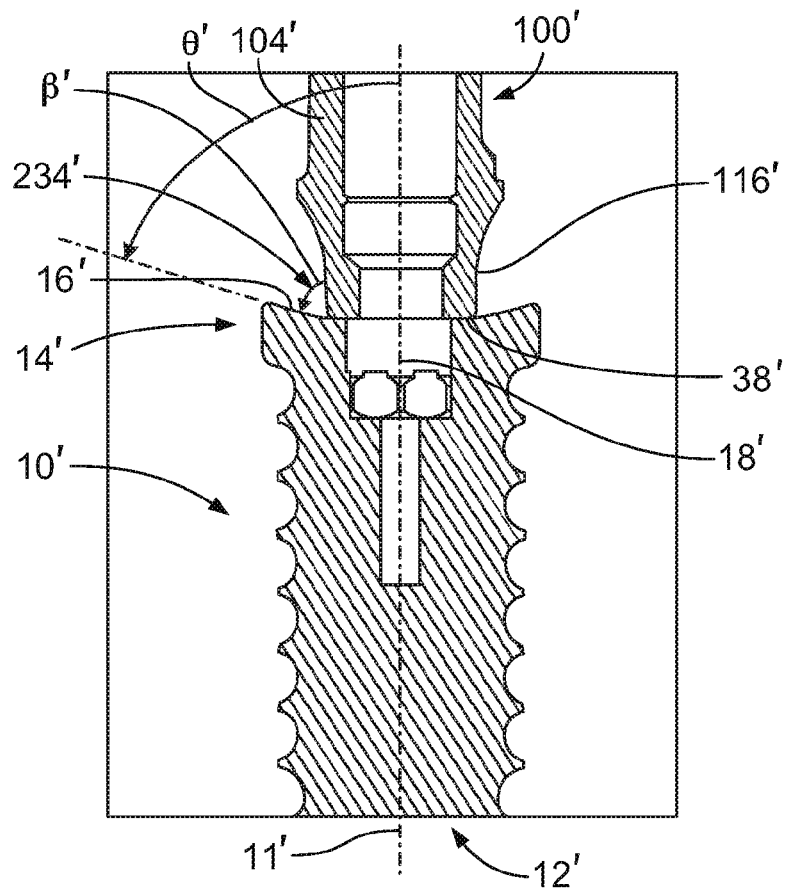
FIG. 4 is a cross-section side view of another embodiment of a dental implant system including an implant and an abutment.

Referring now to FIG. 4, another aspect of the dental implant system according to the present invention is shown. The implant 10' includes a central axis 11', a distal end 12', and a proximal end 14' opposing the distal end 12'. Lateralized surface 16' is located proximate the proximal end 14' of the implant 10'. Adjacent to the lateralized surface 16', an annular vertical support surface 38' supports the abutment 100' and provides a positive limit to the axial movement of the abutment 100' towards the distal end 12'. Like lateralized surface 16, the lateralized surface 16' may be roughened to promote soft tissue growth and attachment and the annular vertical support surface 38' is generally smooth. The lateralized surface 16' is disposed at a negative slope relative to the central axis 11'. The negative slope is defined by an angle θ', which is preferably between about 30° and about 60°, such as about 45°. In another embodiment, the angle θ' is about 75°. The diameter of the interior bore 18' of the implant 10' is smaller than the diameter of the lower end of the transitional surface 110' of the abutment 100'.

The implant 10 and abutment 100 can have interfaces configured in any suitable manner, such as an external polygonal boss on the implant 10 mating with a corresponding polygonal recess on the abutment 100, or other types of internal non-rotational interfaces. For example, the interface of the implant 10 and the abutment 100 may be configured as described in U.S. Pat. No. 7,338,286, which is commonly owned and the disclosure of which is hereby incorporated by reference in its entirety.

Like the embodiment of FIGS. 1-3, the transitional section 116' of the abutment 100' and the lateralized surface 16' of the dental implant 10' define a circumferentially extending recess 234' having a V-shaped cross section for receiving and attachment to the soft tissue. The circumferentially extending recess 234' is substantially open, such that there are no surfaces obstructing or preventing the soft tissue from growing inside the entire surface area of the circumferentially extending recess 234'. The circumferentially extending recess 234' is defined by soft-tissue engagement surfaces forming the angle β' as shown in FIG. 3C. The angle β' may be between about 30° and about 60°, and is preferably about 45°.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A dental implant system, comprising:
a dental implant having a generally cylindrical body and a central axis, the dental implant having a distal end for anchoring in a patient's bone and a proximal end opposing the distal end, the proximal end including a lateralized surface and an abutment-engaging region, the abutment-engaging region being surrounded by the lateralized surface, the lateralized surface defining a soft-tissue attachment interface and being roughened to promote soft-tissue attachment, the lateralized surface being disposed at a negative slope from the perimeter of the cylindrical body toward the distal end relative to the central axis; and
an abutment having an upper portion for supporting a tooth-like prosthesis and a lower portion for engaging the abutment-engaging region of the dental implant, the lower portion having a diameter that is smaller than a diameter of the implant at the proximal end, the lower portion including a first surface with a soft-tissue enhancing material, the first surface of the lower portion being sloped inwardly from the upper portion, the first surface of the lower portion of the abutment and the lateralized surface of the dental implant facing each other and defining a circumferentially extending recess having a V-shaped cross-section for receiving and attachment to the soft tissue.

2. The dental implant system of claim 1, wherein the lateralized surface is roughened by laser treatment, etching, acid etching, mechanical etching, sandblasting, plasma treatment, or any combination thereof.

3. The dental implant system of claim 1, wherein the lateralized surface includes micro-machined grooves.

4. The dental implant system of claim 1, wherein the mean surface roughness of the lateralized surface is between about 1.3 and 3.0 microns.

5. The dental implant system of claim 1, wherein the abutment-engaging region of the dental implant is smooth.

6. The dental implant system of claim 1, wherein the abutment-engaging region includes:
an inner wall of a bore of the implant configured to receive and seal a complimentary outer wall of the abutment;
a horizontal wall adjacent to the inner wall configured to engage a lower end of the abutment to limit axial movement of the abutment; and
an anti-rotational section distal of the horizontal section having a non-round cross-section and configured to engage with a stem of the abutment having a non-round cross-section.

7. The dental implant system of claim 6, wherein the implant further comprises a threaded bore distal of the inner wall, the threaded bore configured to threadably receive a screw holding the abutment on the implant.

8. The dental implant system of claim 1, wherein the dental implant is constructed from titanium, including alloys thereof, and the abutment is constructed from titanium, including alloys thereof, titanium nitride, a ceramic, or a polymer.

9. The dental implant system of claim 1, wherein the first surface is also disposed at a negative slope relative to the central axis.

10. The dental implant system of claim 1, wherein the soft-tissue enhancing material is collagen.

11. The dental implant system of claim 1, wherein the lateralized surface has an outer circumferentially extending surface and an inner circumferentially extending surface, the outer surface being in contact with a collar section of the implant and the inner surface being in contact with the abutment-engaging region.

12. The dental implant system of claim 1, wherein the negative slope is defined by an angle in the range for about 30 to 60° relative to the central axis.

13. The dental implant of claim 1, wherein the lateralized surface is a planar surface that lacks any steps or sharp corners.

14. A dental implant system, comprising:
a dental implant having a generally cylindrical body and a central axis, the dental implant having a distal end for anchoring in a patient's bone and a proximal end opposing the distal end, the proximal end including a lateralized surface and an abutment-engaging region, the abutment-engaging region being surrounded by the lateralized surface, the lateralized surface defining a soft-tissue attachment interface and lacking any sharp angles or corners to prevent abrading of the soft tissue, the lateralized surface being disposed at a negative slope from the perimeter of the cylindrical body toward the distal end relative to the central axis; and
an abutment having an upper portion for supporting a tooth-like prosthesis and a lower portion for engaging the abutment-engaging region of the dental implant, the lower portion including a first surface with at least one soft-tissue enhancing material, the first surface of the lower portion being sloped inwardly from the upper portion, the first surface of the lower portion of the abutment and the lateralized surface of the dental implant facing each other and defining a circumferentially extending recess having a V-shaped cross-section for receiving and attachment to the soft tissue, wherein the dental implant system is platform-switched.

15. The dental implant system of claim 14, wherein the at least one soft-tissue enhancing material is collagen.

16. The dental implant system of claim 14, wherein the abutment includes the first surface with a first soft-tissue enhancing material and a second soft-tissue enhancing material.

17. The dental implant system of claim 14, wherein the lateralized surface is roughened to promote soft tissue attachment.

18. The dental implant system of claim 14, wherein the lateralized surface includes micro-machined grooves.

* * * * *